US00PP14354P39

(12) United States Plant Patent
Coelho

(10) Patent No.: US PP14,354 P3
(45) Date of Patent: Dec. 9, 2003

(54) NECTARINE TREE NAMED 'COELHO'

(50) Latin Name: *Prunus persica nectarina*
Varietal Denomination: Coelho

(75) Inventor: Jerry W. Coelho, Riverdale, CA (US)

(73) Assignee: Terra Linda Farms, Riverdale, CA (US)

( * ) Notice: Subject to any disclaimer, the term of this patent is extended or adjusted under 35 U.S.C. 154(b) by 0 days.

(21) Appl. No.: 09/774,917

(22) Filed: Jan. 30, 2001

(65) Prior Publication Data

US 2002/0104134 P1 Aug. 1, 2002

(51) Int. Cl.[7] ..... A01H 5/00

(52) U.S. Cl. ..... Plt./188

(58) Field of Search ..... Plt./188

*Primary Examiner*—Bruce R. Campell
*Assistant Examiner*—Susan B. McCormick
(74) *Attorney, Agent, or Firm*—Worrel & Worrel

(57) ABSTRACT

A new and distinct variety of nectarine tree which is somewhat remotely similar to the 'July Red' nectarine tree (U.S. Plant Pat. No. 5,663), but from which it is distinguished by producing fruit which are mature for harvesting and shipment approximately two (2) to three (3) days after the fruit produced by the 'July Red' nectarine tree and wherein the fruit is of a high quality, large size, having a white flesh coloration and having a very thin, but distinctive, stripe of yellow skin coloration along the ventral suture of the skin thereof.

1 Drawing Sheet

Latin name of the genus and species of the plant claimed: *Prunus persica nectarina.*

BACKGROUND OF THE NEW VARIETY

The present invention relates to a new and distinct variety of nectarine tree, *Prunus persica nectarina*, which will hereinafter be denominated varietally as the 'Coelho' nectarine tree, and, more particularly, to a nectarine tree which produces full clingstone fruit, which are mature for commercial harvesting and shipment approximately July 14 to July 28 in the San Joaquin Valley of central California.

It is well known that commercially successful varieties of fruit are dependent for their success on a multiplicity of criteria, any one, several, or all of which may be of controlling significance. Similarly, it is frequently the case that the judgment relative to which of these criteria may be decisive in determining the ultimate commercial success of the variety is largely subjective. Nonetheless, certain criteria are considered of particular importance. Such criteria, particularly with respect to tree fruit, may be considered to include ripening date, relative to other commercially successful varieties; size and general quality; skin coloration; flavor; shipping and handling qualities; and the like.

The new variety of the present invention is believed to be a worthy candidate for commercial success based upon such considerations.

ORIGIN AND ASEXUAL REPRODUCTION OF THE NEW VARIETY

The present variety of nectarine tree hereof was discovered by the inventor in his orchard which is located near Laton in the central San Joaquin Valley of California. The inventor discovered the new variety as a newly found seedling. The seed parent of the new variety of the subject invention is believed to be the 'July Red' Nectarine Tree (U.S. Plant Pat. No. 5,663), the pollen parent is unknown. The observed mother sport of the new variety is nine (9)

years old. The fruit of the new variety ripens for commercial harvesting and shipment approximately two (2) to three (3) days after the 'July Red' nectarine tree in the San Joaquin Valley of central California. At the inventor's direction, the new variety hereof was first asexually reproduced in 1994 by grafting bud wood from the original tree onto 'Nemaguard' peach tree rootstock and the resulting trees of the new variety have been observed by the inventor since that time and have been found in all respects to be identical to that of the original tree of the new variety.

DETAILED BOTANICAL DESCRIPTION

Referring more specifically to the botanical details of this new and distinct variety of nectarine tree, the following has been observed under the ecological conditions prevailing at the orchard of origin which is located near Laton in the San Joaquin Valley of central California. All major color code designations are by reference to the *Dictionary of Color,* by Maerz and Paul, First Edition, 1930. Common color names are also occasionally employed.

TREE

Generally:

*Size.*—Height — The tree varies from 9.5 feet (289.56 cm) to 10.5 feet (320.04 cm), including approximately 4.5 feet (137.16 cm) of new growth in late July and was in its 6th leaf of growth propagated on Nemaguard peach rootstock.

*Diameter.*—The tree is approximately 13.5 feet (411.48 cm).

*Vigor.*—Vigorous.

*Chilling requirements.*—The new variety is hardy under typical climatic conditions of the San Joaquin Valley of central California.

*Figure.*—Upright to upright-spreading in form and trained to an open vase system.

*Productivity.*—Productive.

*Pollination.*—No pollination is required.
*Regularity of bearing.*—Regular bearer.

Trunk:
*Size.*—The trunk is of average thickness.
*Diameter.*—6.75 inches (171.45 mm) to 5.75 inches (146.05 mm).
*Bark texture.*—Relatively coarse.
*Color.*—Greyish brown, from (7-L-9) to (7-C-10 Kermanshaw Brown).
*Lenticels.*—Numbers — Numerous large calloused lenticels present throughout the surface.
*Lenticels.*—Form — Oval.
*Lenticels.*—Size — Height — From 1.0 mm (0.04 inches) to 2.5 mm (0.1 inches).
*Lenticels.*—Size — Width — 3 mm (0.12 inches) to 9 mm (0.36 inches).

Branches:
*Size.*—Average thickness. Branch diameter ranges from 4.76 mm (3/16 inches) to 25.4 mm (1.0 inches) depending on location and pruning techniques used.
*Surface texture.*—Branches two years or older have a medium surface texture, usually slightly furrowed.
*Surface texture.*—Current seasons shoots have a glabrous surface texture.
*Internode.*—Length — Normal, ranging from 23 mm (0.92 inches) to 28 mm (1.12 inches) between nodes on fruiting hanger wood.
*Color.*—Mature Branches — Medium brown (15-C-11 Malay Brown) to (14-C-12 Tortoise Brown).
*Color.*—Current Seasons Growth — Exposed surfaces of current season's shoots are often tinged with pink-red (4-E-9) to (4-I-9 Marsh Rose) coloration. Pale green (19-I-5 Kildare Green) to (19-F-6). The color of new shoot tips are bright, shiny green.

Leaves:
*Size.*—Generally — The leaves are from medium to large. Leaf measurements have been taken from leaves located on vigorous, upright, current season's shoots.
*Average length.*—Ranges from 16.7 cm (6.513 inches) to 19.7 cm (7.683 inches), including the petiole.
*Average width.*—Ranges from 4.3 cm (1.677 inches) to 4.9 cm (1.911 inches).
*Thickness.*—Average.
*Form.*—Generally lanceolate.
*Leaf apex.*—Acuminate. Often slightly twisted sideways.
*Color.*—Dorsal surface — Dark green (23-L-7).
*Color.*—Ventral surface — Lighter grey-green (22-K-3).
*Leaf margin.*—Variable, most frequently crenate, but at times approaching serrate. The individual crenations are moderately large and uniform, or regular, in size. The overall leaf margin is moderately undulate.
*Petiole.*—Size — Medium.
*Petiole.*—Length — 11 mm (0.44 inches) to 13 mm (0.52 inches).
*Petiole.*—Thickness — 1.5 mm (0.06 inches) to 2.0 mm (0.08 inches).
*Petiole.*—Color — Pale green (19-I-6), slightly darker within the petiole groove.
*Leaf glands.*—Size — Medium to large.
*Leaf glands.*—Number — Variable.
*Leaf glands.*—Position — Leaf petiole.
*Bloom quality.*—Average abundance to slightly above average. The tree bloom ranges from 75 percent (75%) to 90 percent (90%) and is of high quality.
*Petals.*—Size — Medium.
*Petals.*—Size — Length — 10 mm (0.4 inches) to 13 mm (0.52 inches).
*Petals.*—Size — Width — 10 mm (0.4 inches) to 11 mm (0.44 inches).
*Petal.*—Number — Most frequently five, but occasionally from 3 to 5 small additional obovate form petals can be present.
*Petals.*—Form — The main petals can be variable, from broadly ovate to at times slightly obovate.
*Petals.*—Color — Pink (1-F-2), a darker rose-pink (1-J-3) along the petal margins.
*Petal claw.*—Form — Truncate. The claw is short and moderately broad.
*Petal.*—Margins — Undulate, especially so at the petal apex.
*Petal.*—Apex — Margin — Often ruffled, rounded and at times notched.
*Pedicel.*—Size — Normal.
*Pedicel.*—Size — Length — Averaging 2.0 mm (0.08 inches).
*Pedicel.*—Size — Thickness — Ranging from 1.0 mm (0.04 inches) to 1.5 mm (0.06 inches).
*Pedicel.*—Color — Medium green (19-L-6 Calliste Green).
*Pedicel.*—Surface — Glabrous.
*Floral nectaries.*—Color — Pale green-orange (13-L-8 Buckthorn Brown).
*Calyx.*—Surface — Glabrous and moderately rugose.
*Calyx.*—Color — Maroon (6-J-3 Mineral Red) with areas of green (19-K-4), especially basally.
*Sepal.*—Surface — Pubescent.
*Sepal.*—Size — Medium.
*Sepal.*—Form — Conic.
*Sepal.*—Color — Maroon (6-J-2), at times striped or spotted with areas of green (19-K-3), especially along the margins.
*Anthers.*—Size — Medium. Ranges from 3.18 mm (0.13 inches) to 9.53 mm (0.38 inches), depending on blossom vigor.
*Anther.*—Color — Light tan (11-C-2 Ecru Beige) ventrally and dark red (4-L-9) dorsally.
*Pollen.*—Quantity — Moderate to light.
*Pollen.*—Color — Yellow-gold (10-K-2).
*Filament.*—Length — Ranges from 11 mm (0.44 inches) to 14 mm (0.56 inches) and are usually somewhat shorter than the pistil.
*Filament.*—Color — Pale pink (1-B-1) when young and darkening to a dull purple-rose (3-H-3) with maturity.
*Pistil.*—Length — Ranges from 17 mm (0.68 inches) to 21 mm (0.84 inches), including the ovary.
*Pistil.*—Color — Pale green-yellow (17-H-2).
*Pistil.*—Surface — Glabrous.

FRUIT

Maturity when described: The fruit is described in a firm ripe condition at full commercial maturity. Ripe for commercial harvesting and shipment approximately July 14 to July 28 near Laton in the San Joaquin Valley of central California.

*Stem cavity.*—Width — Ranges from 26 mm (1.04 inches) to 28 mm (1.12 inches).
*Stem cavity.*—Depth — Ranges from 13 mm (0.52 inches) to 15 mm (0.6 inches).

*Stem cavity.*—Length — Ranges from 28 (1.12 inches) to 33 mm (1.32 inches).

*Stem cavity.*—Form — Oval.

*Stem.*—Generally — Medium sized.

*Stem.*—Size — Length — Ranging from 7 mm (0.28 inches) to 11 mm (0.44 inches).

*Stem.*—Size — Thickness — Ranging from 4 mm (0.16 inches) to 5 mm (0.2 inches).

*Stem.*—Color — Olive green (13-J-1), at times with brown streaks present.

*Fruit base.*—Form — Usually slightly truncate. The base angle is variable, from at right angle to the fruit axis to very slightly oblique.

*Fruit apex.*—Form — Rounded with slightly oblique pistil point.

*Pistil point.*—Position — The pistil point is usually depressed within the suture groove, below the height of the shoulders subtending it.

*Weight.*—Large size ranges from 0.25 pounds and up.

Skin:

*Generally.*—Tenacious to the flesh at commercial maturity.

*Thickness.*—Medium, just slightly thicker than average.

*Texture.*—Glabrous.

*Tendency to crack.*—There has been no observed tendency for the skin to split or crack.

*Flavor.*—Slightly acidic.

*Color.*—Variable with from 70 to 95 percent red blush color present.

*Blush.*—Form — Varies from washed to dappled and striped.

Stone:

*Attachment.*—Attachment to the flesh is a full clingstone.

*Fibers.*—Numbers — Attached throughout the stone surface.

*Fibers.*—Length — Medium.

*Size.*—Somewhat variable from medium to large.

*Size.*—Length — Ranges from 36 mm (1.44 inches) to 38 mm (1.52 inches).

*Size.*—Width — Ranges from 26 mm (1.04 inches) to 28 mm (1.12 inches).

*Size.*—Thickness — Ranges from 20 mm (0.8 inches) to 23 mm (0.92 inches).

*Form.*—Generally — Obovate.

*Apex.*—Shape — Acute in form, often with a short dentate tip.

*Color.*—Dry — Tan-brown (14-C-8 Mocha Bisque). A light purplish staining is present over much of the stone surface.

*Kernel.*—Freestone pit.

*Base.*—Shape — Broadly truncate. The base is usually oblique to the stone axis.

*Sides.*—Generally — Variable, from unequal to nearly equal.

*Hilum.*—Size — Large.

*Hilum.*—Form — Generally oval.

*Hilum.*—Collar — Relatively thick which is somewhat raised and often grooved. Both the hilum area and the collar are substantially eroded, especially on the ventral edge.

*Surface.*—Somewhat coarse, with relatively large, irregular pits and grooves present, most deep grooving occurring over the apical shoulder laterally. Finer grooves occur basally over the base itself and the hilum collar.

*Ventral edge.*—Relatively broad. Wings are present but are relatively low, converging apically.

*Ventral edge.*—Width — Ranging from 5 mm (0.2 inches) to 6 mm (0.24 inches) at mid-suture.

*Dorsal edge.*—Somewhat prominent and relatively coarse. A groove is present along the full edge of the suture. The groove is most deep and wide from the stone base up to about mid-suture. From mid-suture to the apex, the groove is thinner and more shallow.

*Ridges.*—Present from the base up to within from 13 mm (0.52 inches) to 15 mm (0.6 inches) of the apex. The ridges are most prominent just above mid-suture and are often cross-cut by distinct grooves.

*Upper dorsal edge.*—Near the apex it is heavily eroded and nearly concave in form.

*Tendency to split.*—No tendency to split has been observed.

*Market use.*—Fresh market.

*Resistance to disease.*—No specific pathogens have been observed resulting in tree loss or degradation.

*Shipping and storage characteristics.*—The fruit holds up well in common storage for up to 28 days.

*Winter hardiness.*—Does well in conditions of 24 degrees Fahrenheit (24° F.) and above, which is the coldest temperature the plant has experienced.

Although the new variety of nectarine tree possesses the described characteristics noted above as a result of the growing conditions prevailing near Laton in the central part of the San Joaquin Valley of California, it is to be understood that variations of the usual magnitude and characteristics incident to changes in growing conditions, irrigation, fertilization, pruning, pest control, climatic variation and the like are to be expected.

I claim:

1. A new and distinct variety of nectarine tree substantially as illustrated and described which is somewhat remotely similar to the 'July Red' nectarine tree (U.S. Plant Pat. No. 5,663), but from which it is distinguished by producing fruit which are mature for commercial harvesting and shipment approximately July 14 to July 28, or about two (2) to three (3) days after, the 'July Red' nectarine tree, and which is characterized as an attractive, early midseason ripening, large size, white fleshed nectarine with high quality and good productivity.

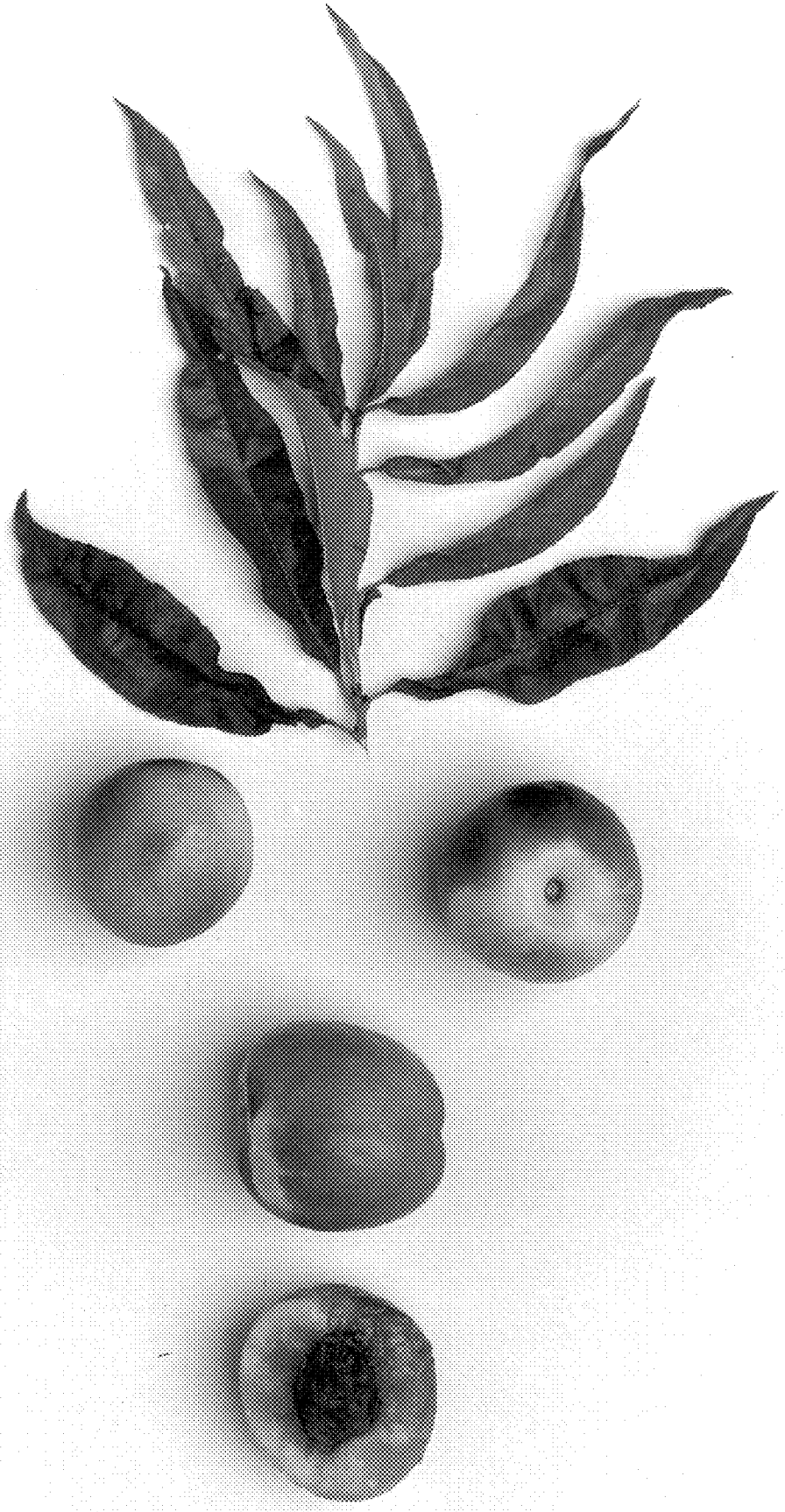

* * * * *